United States Patent
Ramzipoor et al.

(10) Patent No.: US 8,002,789 B2
(45) Date of Patent: Aug. 23, 2011

(54) STRETCH-RESISTANT VASO-OCCLUSIVE DEVICES WITH FLEXIBLE DETACHMENT JUNCTIONS

(75) Inventors: Kamal Ramzipoor, Fremont, CA (US); Like Que, Livermore, CA (US); Jimmy D. Dao, Milpitas, CA (US); Esther Chang, Fremont, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 1611 days.

(21) Appl. No.: 11/140,691

(22) Filed: May 31, 2005

(65) Prior Publication Data

US 2006/0271086 A1 Nov. 30, 2006

(51) Int. Cl.
*A61F 2/06* (2006.01)
(52) U.S. Cl. .................................... 606/200
(58) Field of Classification Search .......... 623/1.23, 623/1.32, 1.44, 1.53, 1.49, 1.5, 1.51, 1.54; 606/191, 200
See application file for complete search history.

(56) References Cited

U.S. PATENT DOCUMENTS

| | | |
|---|---|---|
| 4,994,069 A | 2/1991 | Ritchart et al. |
| 5,122,136 A | 6/1992 | Guglielmi et al. |
| 5,226,911 A | 7/1993 | Chee et al. |
| 5,354,295 A | 10/1994 | Guglielmi et al. |
| 5,382,259 A | 1/1995 | Phelps et al. |
| 5,522,822 A | 6/1996 | Phelps et al. |
| 5,582,619 A | 12/1996 | Ken |
| 5,833,705 A | 11/1998 | Ken et al. |
| 5,853,418 A | 12/1998 | Ken et al. |
| 5,911,737 A * | 6/1999 | Lee et al. .......... 606/209 |
| 5,935,145 A | 8/1999 | Villar et al. |
| 5,976,131 A | 11/1999 | Guglielmi et al. |
| 6,004,338 A | 12/1999 | Ken et al. |
| 6,013,084 A | 1/2000 | Ken et al. |
| 6,033,423 A | 3/2000 | Ken et al. |
| 6,179,857 B1 | 1/2001 | Diaz et al. |
| 6,193,728 B1 | 2/2001 | Ken et al. |
| 6,280,457 B1 | 8/2001 | Wallace et al. |
| 6,287,318 B1 | 9/2001 | Villar et al. |
| 6,296,622 B1 | 10/2001 | Kurz et al. |
| 6,299,627 B1 | 10/2001 | Eder et al. |
| 6,409,721 B1 | 6/2002 | Wheelock et al. |
| 6,425,893 B1 | 7/2002 | Guglielmi |
| 6,533,801 B2 | 3/2003 | Wallace et al. |
| 6,589,236 B2 | 7/2003 | Wheelock et al. |
| 6,620,152 B2 | 9/2003 | Guglielmi |
| 6,623,493 B2 | 9/2003 | Wallace et al. |
| 2002/0099408 A1* | 7/2002 | Marks et al. .......... 606/200 |
| 2004/0098028 A1* | 5/2004 | Martinez .......... 606/200 |

FOREIGN PATENT DOCUMENTS

| | | |
|---|---|---|
| WO | WO 98/37816 | 9/1998 |
| WO | WO 99/40852 | 8/1999 |
| WO | WO 00/72781 A2 | 12/2000 |
| WO | WO 00/74577 A1 | 12/2000 |
| WO | WO 02/096273 A2 | 12/2002 |
| WO | WO 03/094751 A1 | 11/2003 |

* cited by examiner

*Primary Examiner* — Anhtuan T Nguyen
*Assistant Examiner* — Thomas McEvoy
(74) *Attorney, Agent, or Firm* — Vista IP Law Group LLP

(57) ABSTRACT

Disclosed herein are vaso-occlusive devices for forming occluding the vasculature of a patient. More particularly, disclosed herein are vaso-occlusive devices comprising at least one polymer structure and methods of making and using these devices.

21 Claims, 3 Drawing Sheets

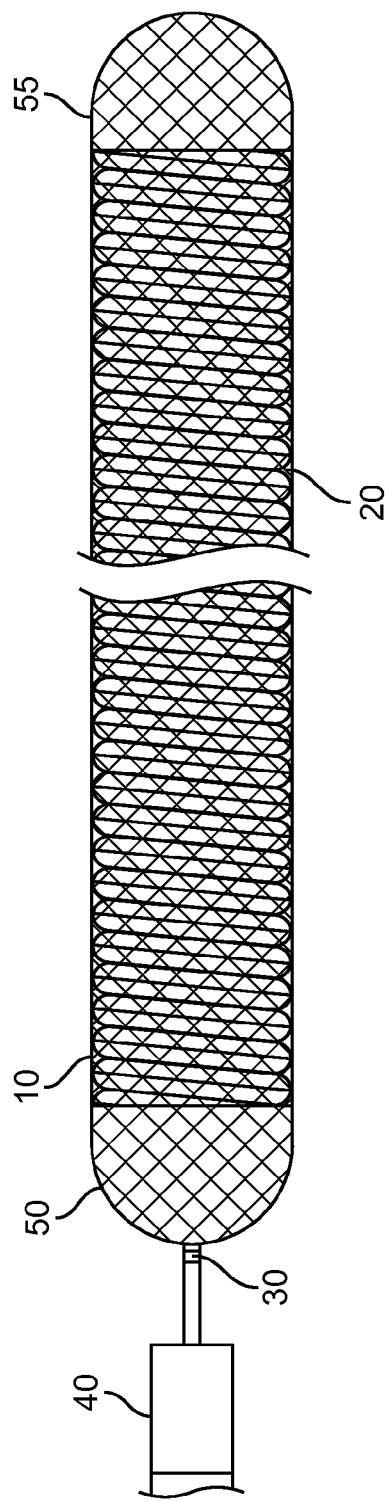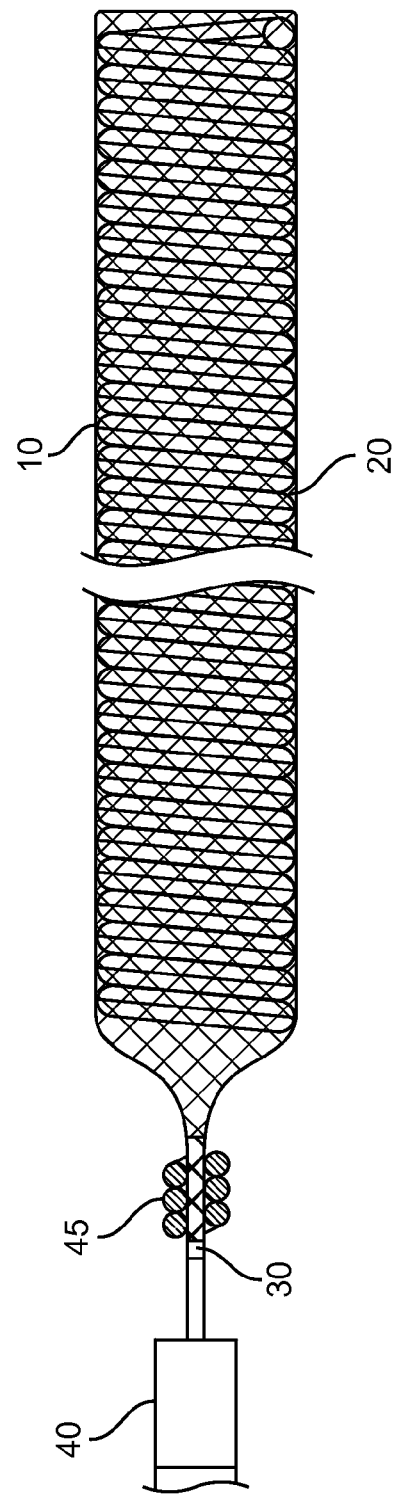

STRETCH-RESISTANT VASO-OCCLUSIVE DEVICES WITH FLEXIBLE DETACHMENT JUNCTIONS

FIELD OF THE INVENTION

Compositions and methods for repair of aneurysms are described. In particular, stretch-resistant vaso-occlusive devices are described, including stretch-resistant vaso-occlusive devices with flexible, articulating detachment junctions.

BACKGROUND

An aneurysm is a dilation of a blood vessel that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings that may be dimensioned to engage the walls of the vessels. (See, e.g., U.S. Pat. No. 4,994,069 to Ritchart et al.).

Coil devices including polymer coatings or attached polymeric filaments have also been described. See, e.g., U.S. Pat. Nos. 5,226,911; 5,935,145; 6,033,423; 6,280,457; 6,287,318; and 6,299,627. For instance, U.S. Pat. No. 6,280,457 describes wire vaso-occlusive coils having single or multi-filament polymer coatings. U.S. Pat. Nos. 6,287,318 and 5,935,145 describe metallic vaso-occlusive devices having a braided polymeric component attached thereto. U.S. Pat. No. 5,382,259 describes braid structures covering a primary coil structure.

In addition, coil designs including stretch-resistant members that run through the lumen of the helical vaso-occlusive coil have also been described. See, e.g., U.S. Pat. Nos. 5,582,619; 5,833,705; 5,853,418; 6,004,338; 6,013,084; 6,179,857; and 6,193,728.

U.S. Pat. Nos. 6,620,152; 6,425,893; 5,976,131 5,354,295; and 5,122,136, all to Guglielmi et al., describe electrolytically detachable embolic devices. U.S. Pat. No. 6,623,493 describes vaso-occlusive member assembly with multiple detaching points. U.S. Pat. Nos. 6,589,236 and 6,409,721 describe assemblies containing an electrolytically severable joint.

However, none of these documents describe stretch-resistant vaso-occlusive devices as described herein, stretch-resistant vaso-occlusive devices that are flexible with respect to the detachment junction, or methods of making and using such devices.

SUMMARY OF THE INVENTION

Thus, this invention includes novel occlusive compositions as well as methods of using and making these compositions.

In one aspect, the invention includes a vaso-occlusive assembly comprising a core element having a proximal end, a distal end and an outer surface, the proximal end of the core element attached to a detachment junction at the distal end of a pusher wire; and at least one polymer structure surrounding a substantial portion of the surface of the core element, the polymeric structure attached to distal end of the core element and to the detachment junction. In certain embodiments, the core element comprises a helically wound coil, for example a wire formed into a helically wound primary shape. In certain embodiments, the helically wound primary shape self-forms into a secondary shape (e.g., cloverleaf shaped, helically-shaped, figure-8 shaped, flower-shaped, vortex-shaped, ovoid, randomly shaped, or substantially spherical shape) upon deployment. The core element is preferably electrolytically detachable from the pusher wire.

In any of the assemblies described herein, the polymer structure may comprise a tubular braid structure, for example a braid comprising at least one polymer selected form group consisting of PET, PLGA, and Nylon. Furthermore, in any of the assemblies described herein, at least one component (e.g., the vaso-occlusive device) may be radioopaque.

In another aspect, the invention includes any of the assemblies described herein further comprising a three-dimensional structure at the distal end of the detachment junction, and wherein the polymer structure at least partially surrounds the three-dimensional structure and further wherein a flexible joint between the three-dimensional structure and the core element is created by the polymer structure. In certain embodiments, the three-dimensional structure at the distal end of the detachment junction is a ball-like structure.

In yet another aspect, the invention includes a method of making an assembly as described herein, the method comprising the steps of (a) securing the polymer structure to the proximal and distal ends of the core element; and (b) attaching the proximal end of the core element to the distal end of a pusher wire, the distal end of the pusher wire comprising an electrolytically detachable junction member. In certain embodiments, step (b) is performed prior to step (a). In other embodiments step (a) and step (b) are performed concurrently. In still further embodiments, step (b) is performed prior to step (a) and further wherein the polymer structure is also secured to the electrolytically detachable junction member. In any of the methods described herein, the core element may comprise a helically wound coil. Furthermore, any of these methods may further comprise the step of forming an end cap at the distal end of the core element (e.g., helically wound coil) from the polymer.

In certain embodiments, the polymer structure is secured to the core element and/or junction member using heat. In other embodiments, the polymer structure is secured to the core element and/or junction member using one or more adhesives. In still further embodiments, the polymer structure is secured to the core element and/or junction member using heat and one or more adhesives.

In yet another aspect, the invention includes a method of at least partially occluding an aneurysm, the method comprising the steps of introducing any of the vaso-occlusive assemblies described herein into the aneurysm and detaching the core element from the detachment junction, thereby deploying the core element into the aneurysm.

Furthermore, any of the assemblies or devices described herein may further include one or more additional components.

These and other embodiments of the subject invention will readily occur to those of skill in the art in light of the disclosure herein.

BRIEF DESCRIPTION OF THE FIGURES

FIG. 1 is a side view depicting an exemplary vaso-occlusive assembly as described herein.

FIG. 2 is a side view depicting another exemplary vaso-occlusive assembly as described herein having an external polymer covering.

DESCRIPTION OF THE INVENTION

Figure 3:
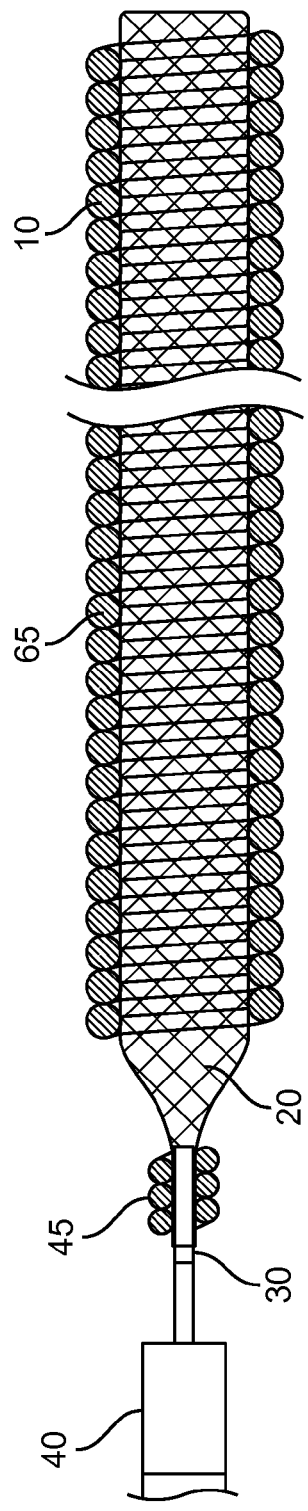
FIG. 3 is a side view depicting another exemplary vaso-occlusive assembly as described herein a first vaso-occlusive coil surrounded by a second vaso-occlusive coil.

Stretch-resistant occlusive (e.g., embolic) compositions are described. The compositions described herein find use in vascular and neurovascular indications and are particularly useful in treating aneurysms, for example small-diameter, curved or otherwise difficult to access vasculature, for example aneurysms, such as cerebral aneurysms. Methods of making and using these vaso-occlusive are also aspects of this invention.

Unlike previously described stretch resistant vaso-occlusive coils, the devices described herein exhibit enhanced stretch resistance (tensile strength) without the need for stretch resistant members within the lumen of the coil device. Instead, stretch resistance is imparted by the use of a polymer structure (e.g., tubular braided structure) covering at least part of the underlying core element (e.g., the coil) and at least part of the detachment junction. Such designs not only exhibit greater stretch resistance than previously described devices, they also exhibit reduced friction and are much simpler to manufacture.

Furthermore, unlike currently available stretch-resistant designs, the devices described herein may be designed to include flexible, articulating detachment junctions. As noted above, implantable devices may be conveniently detached from the deployment mechanism (e.g., pusher wire) by the application of electrical energy, which dissolves a suitable substrate at the selected detachment junction. However, many available electrolytically detachable implants are inflexible in or near the detachment junction. As a result of this inflexibility, the force exerted on the pusher wire by the operator can result in catheter kickback during placement or detachment (i.e., the tip of the catheter is displaced out of the aneurysm when the force exerted on the coil via the pusher wire is transmitted back to the catheter) and/or in inefficient detachment of the coil.

Thus, the devices and assemblies described herein are stretch resistant and, in addition, result in increased flexibility and articulation of the implantable device with respect to the deployment mechanism (e.g., pusher wire and/or catheter). The detachment junction is preferably electrolytically detachable, but may also be adapted to be mechanically detachable (upon movement or pressure) and/or detached upon the application of heat (thermally detachable), the application of radiation, and/or the application of electromagnetic radiation.

Advantages of the present invention include, but are not limited to, (i) the provision of stretch-resistant, low-friction vaso-occlusive devices; (ii) the provision of implantable devices that are articulate around the detachment junction, thereby reducing catheter kickback effects; (iv) the provision of occlusive devices that can be retrieved and/or repositioned after deployment; and (v) cost-effective production of these devices.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise. Thus, for example, reference to a device comprising "a polymer" includes devices comprising of two or more polymers.

The vaso-occlusive devices described herein comprise a core element covered by at least one polymer structure, preferably a braid. The polymer structure may be made up of two or more polymer filaments, for example constructs comprising filamentous elements assembled by one or more operations including coiling, twisting, braiding, weaving or knitting of the filamentous elements.

The polymer(s) making up the structures described herein may be selected from a wide variety of materials. One such example is a suture-type material. Synthetic and natural polymers, such as polyurethanes (including block copolymers with soft segments containing esters, ethers and carbonates), polyethers, polyamides (including nylon polymers and their derivatives), polyimides (including both thermosetting and thermoplastic materials), acrylates (including cyanoacrylates), epoxy adhesive materials (two part or one part epoxy-amine materials), olefins (including polymers and copolymers of ethylene, propylene butadiene, styrene, and thermoplastic olefin elastomers), fluoronated polymers (including polytetrafluoroethylene), polydimethyl siloxane-based polymers, cross-linked polymers, non-cross linked polymers, Rayon, cellulose, cellulose derivatives such nitrocellulose, natural rubbers, polyesters such as lactides, glycolides, trimethylene carbonate, caprolactone polymers and their copolymers, hydroxybutyrate and polyhydroxyvalerate and their copolymers, polyether esters such as polydioxinone, anhydrides such as polymers and copolymers of sebacic acid, hexadecandioic acid and other diacids, or orthoesters may be used.

Thus, the polymer structures described herein may include one or more absorbable (biodegradable) polymers and/or one or more non-absorbable polymers. The terms "absorbable" and "biodegradable" are used interchangeable to refer to any agent that, over time, is no longer identifiable at the site of application in the form it was injected, for example having been removed via degradation, metabolism, dissolving or any passive or active removal procedure. Non-limiting examples of absorbable proteins include synthetic and polysaccharide biodegradable hydrogels, collagen, elastin, fibrinogen, fibronectin, vitronectin, laminin and gelatin. Many of these materials are commercially available. Fibrin-containing compositions are commercially available, for example from Baxter. Collagen containing compositions are commercially available, for example from Cohesion Technologies, Inc., Palo Alto, Calif. Fibrinogen-containing compositions are described, for example, in U.S. Pat. Nos. 6,168,788 and 5,290,552. Mixtures, copolymers (both block and random) of these materials are also suitable.

Preferred biodegradable polymers include materials used as dissolvable suture materials, for instance polyglycolic and/or polylactic acids (PGLA) to encourage cell growth in the aneurysm after their introduction. Preferred non-biodegradable polymers include polyethylene teraphthalate (PET or DACRON™), polypropylene, polytetraflouroethylene, or Nylon materials. Highly preferred are PET or PGLA.

The polymeric structure is used to partially or completely cover a core element. The core element may be made of a variety of materials (e.g., metal, polymer, etc.) and may assume a variety of tubular structures, for examples, braids, coils, combination braid and coils and the like. Thus, although depicted in the Figures described below as a coil, the inner member may be of a variety of shapes or configuration includes, but not limited to, braids, knits, woven structures, tubes (e.g., perforated or slotted tubes), cables, injection-molded devices and the like. See, e.g., U.S. Pat. No. 6,533,801 and International Patent Publication WO 02/096273. The core element preferably changes shape upon deployment, for example change from a constrained linear form to a relaxed, three-dimensional (secondary) configuration. See, also, U.S. Pat. No. 6,280,457.

In a particularly preferred embodiment, the core element comprises at least one metal or alloy. Suitable metals and alloys for the core element include the Platinum Group metals, especially platinum, rhodium, palladium, rhenium, as well as tungsten, gold, silver, tantalum, and alloys of these metals. The core element may also comprise of any of a wide variety of stainless steels if some sacrifice of radio-opacity may be tolerated. Very desirable materials of construction, from a mechanical point of view, are materials that maintain their shape despite being subjected to high stress. Certain "super-elastic alloys" include nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum). Particularly preferred are the alloys described in U.S. Pat. Nos. 3,174,851; 3,351,463; and 3,753,700. Especially preferred is the titanium/nickel alloy known as "nitinol." These are very sturdy alloys that will tolerate significant flexing without deformation even when used as a very small diameter wire. If a super-elastic alloy such as nitinol is used in any component of the device, the diameter of the wire may be significantly smaller than that used when the relatively more ductile platinum or platinum/tungsten alloy is used as the material of construction. These metals have significant radio-opacity and in their alloys may be tailored to accomplish an appropriate blend of flexibility and stiffness. They are also largely biologically inert. In a preferred embodiment, the core element comprises a metal wire wound into a primary helical shape. The core element may be, but is not necessarily, subjected to a heating step to set the wire into the primary shape. The diameter of the wire typically making up the coils is often in a range of 0.0005 and 0.050 inches, preferably between about 0.001 and about 0.004 inches in diameter.

Methods of making vaso-occlusive coils having a linear helical shape and/or a different three-dimensional (secondary) configuration are known in the art and described in detail in the documents cited above, for example in U.S. Pat. No. 6,280,457. Thus, it is further within the scope of this invention that the vaso-occlusive device as a whole or elements thereof comprise secondary shapes or structures that differ from the linear coil shapes depicted in the Figures, for examples, spheres, ellipses, spirals, ovoids, figure-8 shapes, etc. The devices described herein may be self-forming in that they assume the secondary configuration upon deployment into an aneurysm. Alternatively, the devices may assume their secondary configurations under certain conditions (e.g., change in temperature, application of energy, etc.).

The polymeric structures are secured, at least, to the proximal end of the core element. Furthermore, as shown in the Figures, the polymer structure is also in contact with, and preferably secured to, the electrolytically detachable junction at the distal end of the pusher wire. The polymeric structure is also optionally secured near or at the distal end of the core element, for example so as to create an end cap on the distal end of the core element that may ease deployment. Alternatively, the optional end cap may be formed from a different polymer(s) than used to cover the core element.

The polymeric structure(s) may be combined with the core element in any fashion. For example, the polymeric structures may be wound around the core element or, alternatively, may be shaped into a tubular sheath that surrounds the core element. The polymer component may adhere to the core element in one or more locations, for example by heating (melting) of the polymer or by use of adhesives (e.g., EVA) to the polymer or to the core element), heat setting so as to shrink the polymer(s) onto the core element, or by other suitable means. The polymer component may completely cover the core element (as shown in FIG. 1B) or may be added to the core element such that one or more regions of the core element are not covered.

It will be apparent that the process used to attach the polymer to the core element will depend on the nature of the polymer. For example, it will be preferable not to heat certain polymers (e.g., PGLA) as heating may cause degradation of PGLA. Furthermore, the polymeric component may be added to the core element before or after the core element is shaped into a primary and/or secondary configuration.

The polymeric component may be added before or after the core element is attached to a detachable junction. Typically, the core element is attached to a detachment junction at its proximal end. See, also, Examples. Methods of connecting a core element to a pusher wire having an electrolytically detachable junction are well known and described for example in U.S. Pat. Nos. 6,620,152; 6,425,893; 5,976,131 5,354,295; and 5,122,136. It will be apparent that the detachment junction may also include additional polymers to which the core element and polymer coverings are secured. For example, when the core element is secured to the detachment junction prior to addition of the polymeric structure, the distal end of the detachment junction may comprise a polymer such as PET. The use of the polymer structures attached to known vaso-occlusive devices (core elements) as described herein results in much less friction upon delivery and/or deployment and, in addition, increases the stretch-resistance (tensile strength) of the devices.

Depicted in the Figures are exemplary embodiments of the present invention in which the core element is depicted as a helically wound metallic coil. It will be appreciated that the drawings are for purposes of illustration only and that other implantable devices can be used in place of embolic coils, for example, stents, filters, and the like. Furthermore, although depicted in the Figures as embolic coils, the embolic devices may be of a variety of shapes or configuration including, but not limited to, open and/or closed pitch helically wound coils, braids, wires, knits, woven structures, tubes (e.g., perforated or slotted tubes), injection-molded devices and the like. See, e.g., U.S. Pat. No. 6,533,801 and International Patent Publication WO 02/096273. It will also be appreciated that the devices and assemblies can have various configurations as long as they are stretch resistant and/or exhibit the required flexibility.

FIG. 1 is a schematic depicting an exemplary stretch-resistant device as described herein. The device comprises a helically wound core element 10 covered by a tubular polymeric braid structure 20. Also shown in FIG. 1 is detachment junction 30 and pusher wire 40. The tubular polymer braid 20 is secured to the proximal and distal ends of the core element 10 and to the distal region of the detachment junction 30.

As shown in FIG. 1, the device optionally includes end caps 50, 55, to ease the potential of the core element to cause trauma to the target vessel. Optional end caps 50, 55 are depicted in FIG. 1 as formed from polymer braid 20. Alternatively, optional end caps 50, 55 may be formed from different polymers or from the core element. One or both of the end caps may be present.

FIG. 2 shows an embodiment in which the tubular braid 20 is secured to the distal end of the detachment region 30 using an electrically insulated coil 45 structure. It will be apparent that the polymeric braid can be secured near the distal end of the detachment region by any suitable means, for example by melting or gluing. Furthermore, the detachment region 30 may further include an additional polymer on its distal end.

FIG. 3 shows an exemplary embodiment similar to FIG. 2 but further comprising a second helically wound vaso-occlusive device (coil) 65 surrounding the helically wound core element 10 (and tubular braid 20). As shown in FIG. 2, it is preferred that the second coil 65 is shorter than or an equivalent length as the core element 10. In certain instances, the second coil 65 may be longer than the core element 10, so long as it does not restrict flexibility of the core element 10 with respect to the detachment zone 30. Second coil 65 may be wholly or partially electrically insulated or wholly or partially electrically conductive.

Like the embodiment in FIG. 3, the tubular braid 20 of the embodiment shown in FIG. 3 is secured near the distal end of the detachment region 30 using an electrically insulated coil 45 structure. Furthermore, although depicted in FIG. 3 as separate components, it will be apparent that the second outermost helically wound vaso-occlusive device 65 and the electrically insulated coil 45 structure securing the tubular braid 20 to the detachment zone 30 can be a single component, formed, for example, by helically winding an electrically insulated wire in the configuration shown in FIG. 3. When second device 65 and securing coil 45 are a single component, one or more regions of the second device 65 may have electrical insulation removed therefrom.

In any of the exemplary devices described herein, the polymeric braid may be loaded onto core element before or after the core element is secured near the distal end of the detachment zone.

As noted above, stretch-resistant vaso-occlusive devices as described herein are conveniently detached from the deployment mechanism (e.g., pusher wire) by the application of electrical energy, which dissolves a suitable substrate at the selected detachment junction. The present invention also relates to flexible detachment junctions, which result in reduced catheter kickback and more efficient deployment. In particular, flexibility at the detachment zone may be imparted by attaching the polymer to the detachment junction in such a way that the stretch-resistant device is free to pivot with respect to the pusher wire.

Figure 4:
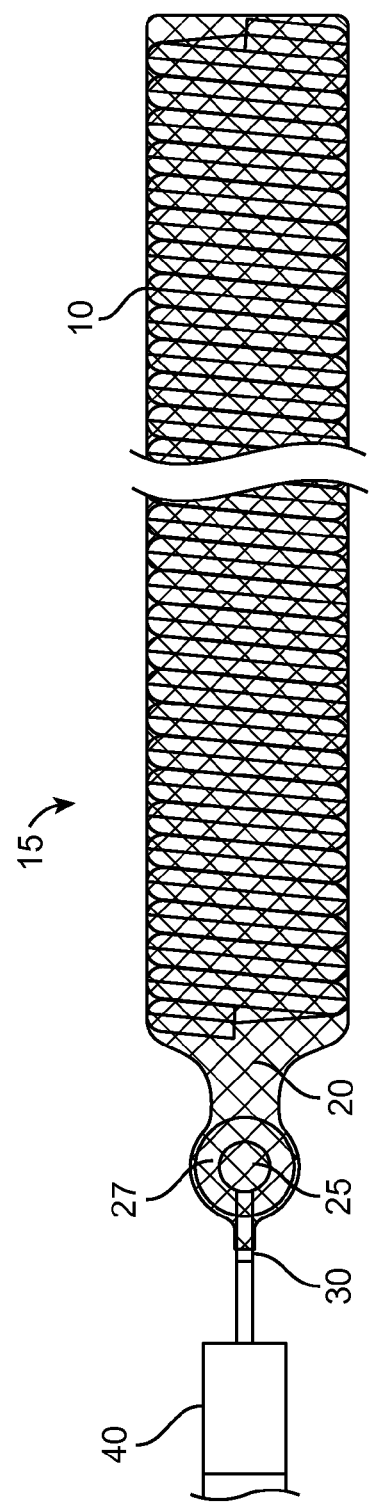
FIG. 4 is a side view depicting yet another exemplary vaso-occlusive assembly as described herein in having a ball-like structure positioned near the distal end of the detachment zone.

FIG. 4 depicts an exemplary stretch resistant device 15 in which pusher wire 40 comprises a ball-like structure 25 at its distal end. The ball-like structure 25 is covered by an electrically insulated material 27. The stretch resistant device 15 includes a core element 10 and polymer covering 20. The polymer covering 20 covers the core element 10 and the distal portion of the detachment junction 30 of the pusher wire 40 including the ball-like structure 25 and insulating material 27. As a result of covering the distal end of the detachment junction 30 with the polymer structure 20 used to cover the core element 10, a flexible, articulating joint is created between the core element 10 and detachment junction 30.

Figure 5A:
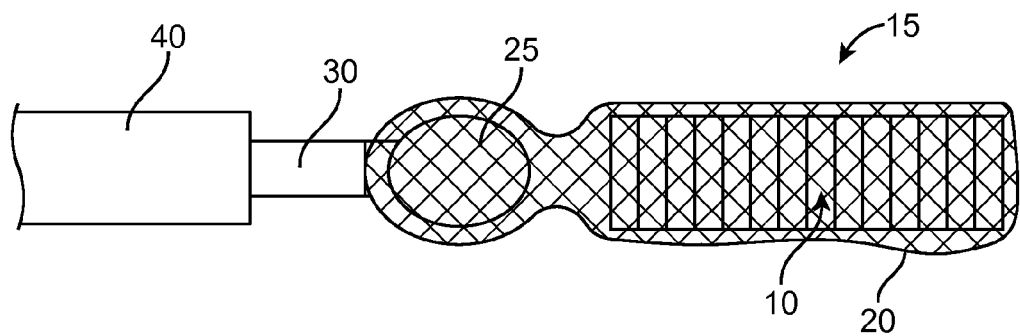
FIGS. 5A and 5B are side views depicting another exemplary vaso-occlusive assembly as described herein including a flexible joint created by the polymer structure when it is placed over the core element and over distal end of the pusher wire.
Figure 5B:
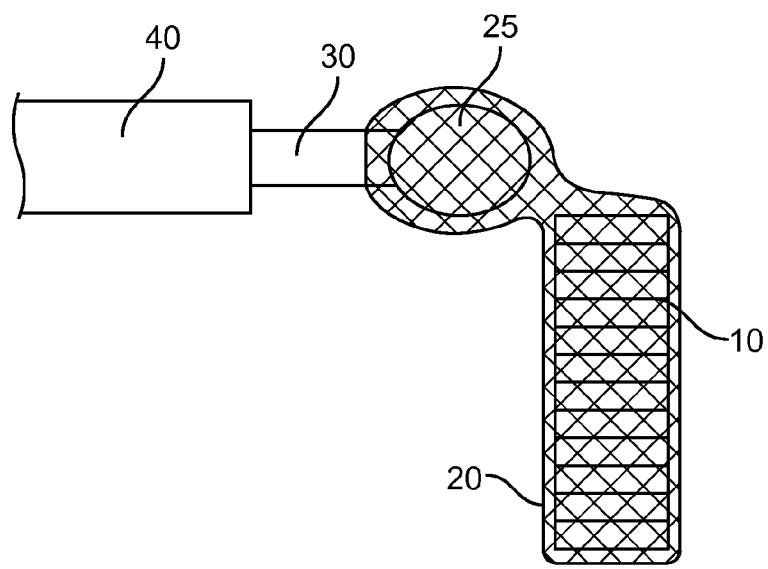

FIG. 5A is a schematic showing an embodiment similar to the one depicted in FIG. 4 in a linear configuration. FIG. 5B shows how the flexible joint allows the core element 10 to pivot with respect to the pusher wire 40.

Although illustrated in the Figures as a ball-like structure, it will be apparent that flexibility may be imparted by the inclusion of virtually any three-dimensional structure, or in some cases, simply by using the distal end of the pusher wire 40, so long as a flexible joint is created by from the polymer coating 20. Non-limiting examples of suitable three-dimensional structures include ball-like structures, other spherical shapes, ovoid shapes, cubes, etc. It will also be apparent that one or more additional polymers may be included at one or more regions of the assembly, for example at the distal end of the detachment junction 30.

Furthermore, as noted above, the polymer may be combined with the core element before, concurrently or after the core element combining with the pusher wire having a detachment junction at its distal end. In other words, the core element may be combined with the pusher wire using standard techniques to form a GDC detachment junction and, subsequently, a polymer structure may be applied to the core element-pusher wire assembly. Alternatively, the core element may be first combined with a polymer structure, which is subsequently combined with the pusher wire to form a GDC junction. Then again, the core element and pusher wire may be combined using the polymer structure to form the GDC junction. The polymer structure may be combined with the core element and detachment junction using any of the methods described above, including, but not limited to, melting, adhesives and/or heat shrinking.

One or more of the components of the devices described herein (e.g., polymer covering, core element) may also comprise additional components (described in further detail below), such as co-solvents, plasticizers, radio-opaque materials (e.g., metals such as tantalum, gold or platinum), coalescing solvents, bioactive agents, antimicrobial agents, anti-thrombogenic agents, antibiotics, pigments, radiopacifiers and/or ion conductors which may be coated using any suitable method or may be incorporated into the element(s) during production. In addition, lubricious materials (e.g., hydrophilic) materials may be used to coat one or more members of the device to help facilitate delivery. Cyanoacrylate resins (particularly n-butylcyanoacrylate), particular embolization materials such as microparticles of polyvinyl alcohol foam may also be introduced into the intended site after the inventive devices are in place. Furthermore, previously described fibrous braided and woven components (U.S. Pat. No. 5,522, 822) may also be included, for example surrounding the polymeric structure-covered core elements described herein.

One or more bioactive materials may also be included. See, e.g., co-owned U.S. Pat. No. 6,585,754 and WO 02/051460. The term "bioactive" refers to any agent that exhibits effects in vivo, for example a thrombotic agent, an anti-thrombotic agent (e.g., a water-soluble agent that inhibits thrombosis for a limited time period, described above), a therapeutic agent (e.g., chemotherapeutic agent) or the like. Non-limiting examples of bioactive materials include cytokines; extracellular matrix molecules (e.g., collagen); trace metals (e.g., copper); and other molecules that stabilize thrombus formation or inhibit clot lysis (e.g., proteins or functional fragments of proteins, including but not limited to Factor XIII, $\alpha_2$-antiplasmin, plasminogen activator inhibitor-1 (PAI-1) or the like). Non-limiting examples of cytokines which may be used alone or in combination in the practice of the present invention include, basic fibroblast growth factor (bFGF), platelet derived growth factor (PDGF), vascular endothelial growth factor (VEGF), transforming growth factor beta (TGF-β) and the like. Cytokines, extracellular matrix molecules and thrombus stabilizing molecules (e.g., Factor XIII, PAI-1, etc.) are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additionally, bioactive polypeptides can be synthesized recombinantly as the sequences of many of these molecules are also available, for example, from the GenBank database. Thus, it is intended that the invention include use of DNA or RNA encoding any of the bioactive molecules. Cells (e.g., fibroblasts, stem cells, etc.) can also be included. Such cells may be genetically modified. Furthermore, it is intended, although not always explicitly stated, that molecules having similar biological activity as wild-type or purified cytokines, extracellular matrix molecules and thrombus-stabilizing proteins (e.g., recombinantly produced or mutants thereof) and nucleic acid encoding these molecules are intended to be used within the spirit and scope of the invention. Further, the amount and concentration of liquid embolic and/or other bioactive materials useful in the practice of the invention can be readily determined by a skilled operator and it will be understood that any combination of materials, concentration or dosage can be used, so long as it is not harmful to the subject.

The devices described herein are often introduced into a selected site using the procedure outlined below. This procedure may be used in treating a variety of maladies. For instance in the treatment of an aneurysm, the aneurysm itself will be filled (partially or fully) with the compositions described herein.

Conventional catheter insertion and navigational techniques involving guidewires or flow-directed devices may be used to access the site with a catheter. The mechanism will be such as to be capable of being advanced entirely through the catheter to place vaso-occlusive device at the target site but yet with a sufficient portion of the distal end of the delivery mechanism protruding from the distal end of the catheter to enable detachment of the implantable vaso-occlusive device. For use in peripheral or neural surgeries, the delivery mechanism will normally be about 100-200 cm in length, more normally 130-180 cm in length. The diameter of the delivery mechanism is usually in the range of 0.25 to about 0.90 mm. Briefly, occlusive devices (and/or additional components) described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the embolics (e.g. vaso-occlusive members and/or liquid embolics and bioactive materials) which cause formation of an emboli and, at some later time, is at least partially replaced by neovascularized collagenous material formed around the implanted vaso-occlusive devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared. For instance, if a guidewire has been used to position the catheter, it is withdrawn from the catheter and then the assembly, for example including the absorbable vaso-occlusive device at the distal end, is advanced through the catheter.

Once the selected site has been reached, the vaso-occlusive device is extruded, for example by loading onto a pusher wire. Preferably, the vaso-occlusive device is loaded onto the pusher wire via an electrolytically cleavable junction (e.g., a GDC-type junction that can be severed by application of heat, electrolysis, electrodynamic activation or other means). Additionally, the vaso-occlusive device can be designed to include multiple detachment points, as described in co-owned U.S. Pat. Nos. 6,623,493 and 6,533,801 and International Patent publication WO 02/45596. They are held in place by gravity, shape, size, volume, magnetic field or combinations thereof.

EXAMPLE

To test the stretch-resistant properties of the devices described herein, the following experiments were performed. Two-inch long core platinum linear coils (0.00175" wire diameter and 0.006 inner diameter of coil) were covered with either a PET braid (12 end, 80° braiding angle, 0.013" (Secant)) or a PLGA braid (16 end, high braiding angle, 0.013" (Secant)).

For the PET covered coil, the PET tubular braid was loaded over the coil and melted to the distal and proximal ends. A short PET plug was inserted into the Pt coil to increase bonding strength. The PET at the proximal end of the Pt coil was then joined to an electrolytically detachable junction on the distal end of a pusher wire using standard GDC processing techniques.

For the PGLA covered coil, a platinum coil was joined to an electrolytically detachable junction on the distal end of a pusher wire using standard GDC processing techniques, using a PET junction. Subsequently, the PGLA tubular braid was slid over the Pt coil and glued to the distal end of the coil with Dymax 1128 UV curable adhesive. The proximal end of the PGLA tubular braid was also glued to the PET junction (at the proximal end of the coil) using the same adhesive.

Tensile strength of the PET- and PGLA-covered was compared to currently available stretch resistant coil designs available as GDC™-10 Soft SR coils from Boston Scientific. Currently available stretch-resistant designs included sutures through the lumen of a helically wound coil. Tensile testing was conducted using equipment available from Instron®. In particular, tensile tests as between the distal portion of the coil 0.5 inches from the tip and the pusher wire at 2 inches/minute were conducted. Results of 5 separate experiments are shown in Table 1.

TABLE 1

| Designs | Sample # | Tensile Strength (lbs) | Average | Standard Deviation |
|---|---|---|---|---|
| PET tubular melt | 1 | 0.3311 | | |
| | 2 | 0.3303 | | |
| | 3 | 0.3412 | | |
| | 4 | 0.2842 | | |
| | 5 | 0.3786 | 0.333 | 0.034 |
| PGLA tubular glue | 1 | 0.1264 | | |
| | 2 | 0.4786 | | |
| | 3 | 0.4417 | | |
| | 4 | 0.3195 | | |
| | 5 | 0.1956 | 0.312 | 0.152 |
| Current GDC Stretch | 1 | 0.0745 | | |
| Resistant Designs | 2 | 0.114 | | |
| (Member through | 3 | 0.0547 | | |
| Lumen) | 4 | 0.0379 | | |
| | 5 | 0.1654 | 0.089 | 0.051 |

Thus, the devices described herein exhibit approximately 3 to 3.5 fold increased stretch resistance as compared to currently available stretch resistant designs (inner suture or thread designs). In particular, the PET braid melt design improved stretch-resistance by approximately 3.5 fold over current designs, while the PGLA design (glued) improved stretch-resistance by approximately 3 fold over current designs.

Modifications of the procedure and vaso-occlusive devices described above, and the methods of using them in keeping with this invention will be apparent to those having skill in this mechanical and surgical art. These variations are intended to be within the scope of the claims that follow.

What is claimed is:

1. A vaso-occlusive assembly comprising
    a core element having a proximal end, a distal end and an outer surface; and
    at least one polymer structure surrounding a substantial portion of the surface of the core element, the polymeric structure attached to distal end of the core element and to a detachment junction,
    wherein the polymeric structure secures the core element to the detachment junction prior to deployment,
    wherein the core element is electrolytically detachable from a pusher wire.

2. The vaso-occlusive assembly of claim 1, wherein the core element comprises a helically wound coil.

3. The vaso-occlusive assembly of claim 1, wherein the polymer structure comprises a tubular braid structure.

4. The vaso-occlusive assembly of claim 3, wherein the braid comprises at least one polymer selected form group consisting of PET, PLGA, and Nylon.

5. The vaso-occlusive assembly of claim 1, wherein the core element comprises a wire formed into a helically wound primary shape.

6. The vaso-occlusive assembly of claim 5, where the core element has a secondary shape that self-forms upon deployment.

7. The vaso-occlusive assembly of claim 6, where the secondary shape is selected from the group consisting of clover-leaf shaped, helically-shaped, figure-8 shaped, flower-shaped, vortex-shaped, ovoid, randomly shaped, and substantially spherical.

8. The vaso-occlusive assembly of claim 1, wherein the device is radioopaque.

9. The vaso-occlusive assembly of claim 1, wherein the core element is electrolytically detachable from a pusher wire.

10. The vaso-occlusive assembly of claim 1, further comprising a three-dimensional structure at the distal end of the detachment junction, wherein the polymer structure at least partially surrounds the three-dimensional structure and further wherein a flexible joint between the three-dimensional structure and the core element is created by the polymer structure.

11. The vaso-occlusive assembly of claim 10, wherein the three-dimensional structure at the distal end of the detachment junction is a ball-like structure.

12. A method of making a vaso-occlusive assembly according to claim 1, comprising the steps of
    (a) securing a polymer structure to the proximal and distal ends of the core element; and
    (b) attaching the polymer structure at the proximal end of the core element to the distal end of a pusher wire,
    wherein the distal end of the pusher wire comprises an electrolytically detachable junction member.

13. The method of claim 12, wherein step (a) is performed prior to step (b).

14. The method of claim 12, wherein step (a) and step (b) are performed concurrently.

15. The method of claim 12, wherein step (b) is performed prior to step (a) and further wherein the core element is also secured to the electrolytically detachable junction member.

16. The method of claim 12, wherein the core element comprises a helically wound coil.

17. The method of 16, further comprising the step of forming an end cap at the distal end of the helically wound coil from the polymer.

18. The method of claim 12, wherein the polymer structure is secured to the core element and/or junction member using heat.

19. The method of claim 12, wherein the polymer structure is secured to the core element and/or junction member using one or more adhesives.

20. The method of claim 12, wherein the polymer structure is secured to the core element and/or junction member using heat and one or more adhesives.

21. A method of at least partially occluding an aneurysm, the method comprising the steps of introducing a vaso-occlusive assembly according to claim 1 into the aneurysm and detaching the polymeric structure from the detachment junction, thereby deploying the core element into the aneurysm.

* * * * *